US00PP11942P2

(12) United States Plant Patent
Booman

(10) Patent No.: US PP11,942 P2
(45) Date of Patent: Jun. 19, 2001

(54) BEGONIA PLANT NAMED 'TUCSON BONFIRE'

(76) Inventor: James Lawrence Booman, 2302 Bautista Ave., Vista, CA (US) 92084

( * ) Notice: Subject to any disclaimer, the term of this patent is extended or adjusted under 35 U.S.C. 154(b) by 0 days.

(21) Appl. No.: 09/375,788

(22) Filed: Aug. 17, 1999

(51) Int. Cl.[7] ..... A01H 5/00

(52) U.S. Cl. ..... Plt./343

(58) Field of Search ..... Plt./343

*Primary Examiner*—Bruce A. Campell
*Assistant Examiner*—Anne Marie Grünberg
(74) *Attorney, Agent, or Firm*—C. A. Whealy

(57) ABSTRACT

A new and distinct cultivar of Rex Begonia plant named 'Tucson Bonfire', characterized by its uniform growth habit; moderate plant vigor; no requirement for winter dormancy; and interesting and attractive leaf coloration and pattern.

1 Drawing Sheet

BACKGROUND OF THE INVENTION

The present invention relates to a new and distinct cultivar of Begonia plant, botanically known as *Begonia rex* hybrid, commercially known as Rex Begonia, and hereinafter referred to by the name 'Tucson Bonfire'.

The new Rex Begonia was discovered and selected by the Inventor in a controlled environment in Vista, Calif., in August, 1995, within a large group of seedling progeny from multiple crossings of unidentified selections of *Begonia rex* hybrids.

The selection of this plant was based on its uniform growth habit, moderate plant vigor, and attractive foliage coloration and pattern.

Asexual reproduction of the new Rex Begonia by leaf cuttings taken in a controlled environment in Vista, Calif., has shown that the unique features of this new Rex Begonia are stable and reproduced true to type in successive generations.

SUMMARY OF THE INVENTION

The cultivar 'Tucson Bonfire' has not been observed under all possible environmental conditions. The phenotype may vary somewhat with variations in environment such as temperature, daylength and light intensity, without, however, any variance in genotype.

The following traits have been repeatedly observed and are determined to the the unique characteristics of 'Tucson Bonfire'. These characteristics in combination distinguish 'Tucson Bonfire' as a new and distinct Rex Begonia:

1. Uniform growth habit.
2. Moderate plant vigor.
3. Does not require winter dormancy.
4. Interesting and attractive leaf coloration and pattern.

In side-by-side comparions conducted by the Inventor in Vista, Calif., plants of the new Rex Begonia differ from plants of the nonpatented cultivar 'Merry Christmas Corkscrew' in the following characteristics:

1. Plants of the new Rex Begonia grow more rapidly than plants of the cultivar 'Merry Christmas Corkscrew'.
2. Leaves of plants of the new Rex Begonia are larger and more brightly colored than leaves of plants of the culitvar 'Merry Christmas Corkscrew'.

3. Leaves of plants of the new Rex Begonia do not have a "corkscrew" formation whereas leaves of plants of the cultivar 'Merry Christmas Corkscrew' have a "corkscrew" formation.
4. Plants of the new Rex Begonia do not require a winter dormancy period whereas plants of the cultivar 'Merry Christmas Corkscrew' do require a winter dormancy period.

In side-by-side comparisons conducted by the Inventor in Vista, Calif., plants of the new Rex Begonia differ from plants of the nonpatented cultivar 'Lillium' in the following characteristics:

1. Plants of the new Rex Begonia grow more rapidly than plants of the cultivar 'Lillium'.
2. Leaves of plants of the new Rex Begonia are larger, flatter and are more brightly colored that leaves of plants of the cultivar 'Lillium'.
3. Plants of the new Rex Begonia do not require a winter dormancy period whereas plants of the cultivar 'Lillium' do require a winter dormancy period.

BRIEF DESCRIPTION OF THE PHOTOGRAPH

The accompanying colored photograph illustrates the overall appearance of the new Rex Begonia, showing the colors as true as it is reasonably possible to obtain in colored reproductions of this type. The photograph comprises a top perspective view of a typical plant of 'Tucson Bonfire'. Foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown during the spring in Vista, Calif., under conditions which approximate commercial practice. Plants used for this description were grown in 15-cm containers for about 3 months.

Botanical classification: *Begonia rex* hybrid cultivar 'Tucson Bonfire'.

Commercial classification: Rex Begonia.

Parentage: Chance seedling of multiple crossings of unidentified selections of *Begonia rex* hybrids.

Propagation:

*Type.*—Leaf cuttings.

*Time to initiate roots, summer.*—About 56 days at 21° C.

*Time to initiate roots, winter.*—About 56 days at 21° C.

*Time to develop roots, summer.*—About 84 days at 21° C.

*Time to develop roots, winter.*—About 98 days at 21° C.

*Rooting habit.*—Fine, fibrous and well-branched.

Plant description:

*Plant form.*—Rosette; compact; dense and outwardly arching potted plant; freely basal branching with good leaf petiole strength.

*Vigor.*—Moderate.

*Plant height, soil surface to top of leaf canopy.*—About 22.5 cm.

*Plant width.*—About 51 cm.

*Leaves.*—Arrangement: Simple. Length: Petiole to apex: About 16.5 cm. Base to apex: About 21 cm. Width: About 15 cm. Shape: Asymmetrical, oblique to ovate. Apex: Acute. Base: Asymmetrically cordate. Margin: Pectinate: irregularly undulate. Texture: Leathery, rugose; pubescence on lower surface veins. Color: Young foliage, upper surface: Margin: Dark brown, 200A, occasional spots of 186C. Central venal areas: 200A shading to 200B to 200C; becoming close to 143A. Blade: 186B to 186C with hint of metallic 186A; merging with close to 148D. Young foliage, lower surface: Margin: 187A. Central venal areas: 187A, spreading to close to 183B. Background: 148C. Mature, fully expanded, foliage, upper surface: Margin: Dark brown, 200A. Central venal areas: 200A, extending to 200B to 200C, then to blotches of close to 146A. Blade: Large blotches of 183C to 183D bordering the green and merging with 191C and 148C near apex. Veins: Close to 183A. Mature, fully expanded, foliage, lower surface: Margin: 187A. Blade: 183A to 183B blending to 148C. Veins: Close to 187A; reticulate.

*Petioles.*—Length: About 11.5 cm. Diameter: About 7 mm. Shape: Longitudinally grooved. Texture: Pubescent. Color: 183A.

*Stipules.*—Length: About 19.5 mm. Diameter at base: About 9 mm. Shape: Subulate. Color: 178A to 178B.

Flower description:

*Flowering habit.*—Male flowers, single with one whorl of four tepals. Female flowers, semi-double with three tepals interior to outer whorl of five tepals. Usually about five or six flowers per cyme. Flowers persistent.

*Natural flowering season.*—Plants will flower continuously, but typically plants flower more abundantly during the spring and summer.

*Flowers.*—Shape: Rounded; somewhat cup-shaped. Diameter: About 2.5 cm. Depth (height): About 1.4 cm. Fragrance: None.

*Flower buds.*—Shape: Spherical; bulbous with marginal lip. Length: About 1.4 cm. Diameter: About 1.5 cm. Color: 68D.

*Tepals.*—Arrangement: Rosette. Length: About 1.5 cm. Width: About 1.3 cm. Shape: Ovate with obtuse apex. Margin: Entire. Texture: Smooth, waxy; iridescent, translucent. Color: When opening, upper surface: 54D to 63D. When opening, lower surface: 54C and 39A; linear stripe, 67B. Fully opened, upper surface: 68D to 65B with translucent veins. Fully opened, lower surface: 63D fusing basally with 63C and 39A.

*Peduncles.*—Angle: About 45° from vertical. Length: About 3.5 cm. Diameter: About 3 mm. Strength: Firm. Texture: Smooth, waxy. Color: Close to 178A.

*Pedicels.*—Angle: About 75° from vertical. Length: About 1.6 cm. Diameter: About 2 mm. Strength: Moderate. Texture: Smooth, waxy. Color: 178A to 178B.

*Reproductive organs.*—Male flowers: Stamen quantity: About 76, globose mass. Anther shape: Rhomboidal; lower sides curved inwardly. Anther length: About 1.9 mm. Filament length: About 1 mm. Anther color: Close to 17A. Pollen: Not observed. Female flowers: Pistil length: About 2 cm. Stigma shape: Funnel; bilobate. Stigma color: 171C; margin, 164B to 164C. Ovary: Inferior; three-winged; one large top wing and two lower wings; both surfaces, close to 34A to 34B.

Disease resistance: Resistance to diseases common to Rex Begonia has not been determined.

Seed production: Seed production has not been observed.

It is claimed:

1. A new and distinct cultivar of Rex Begonia plant named 'Tucson Bonfire', as illustrated and described.

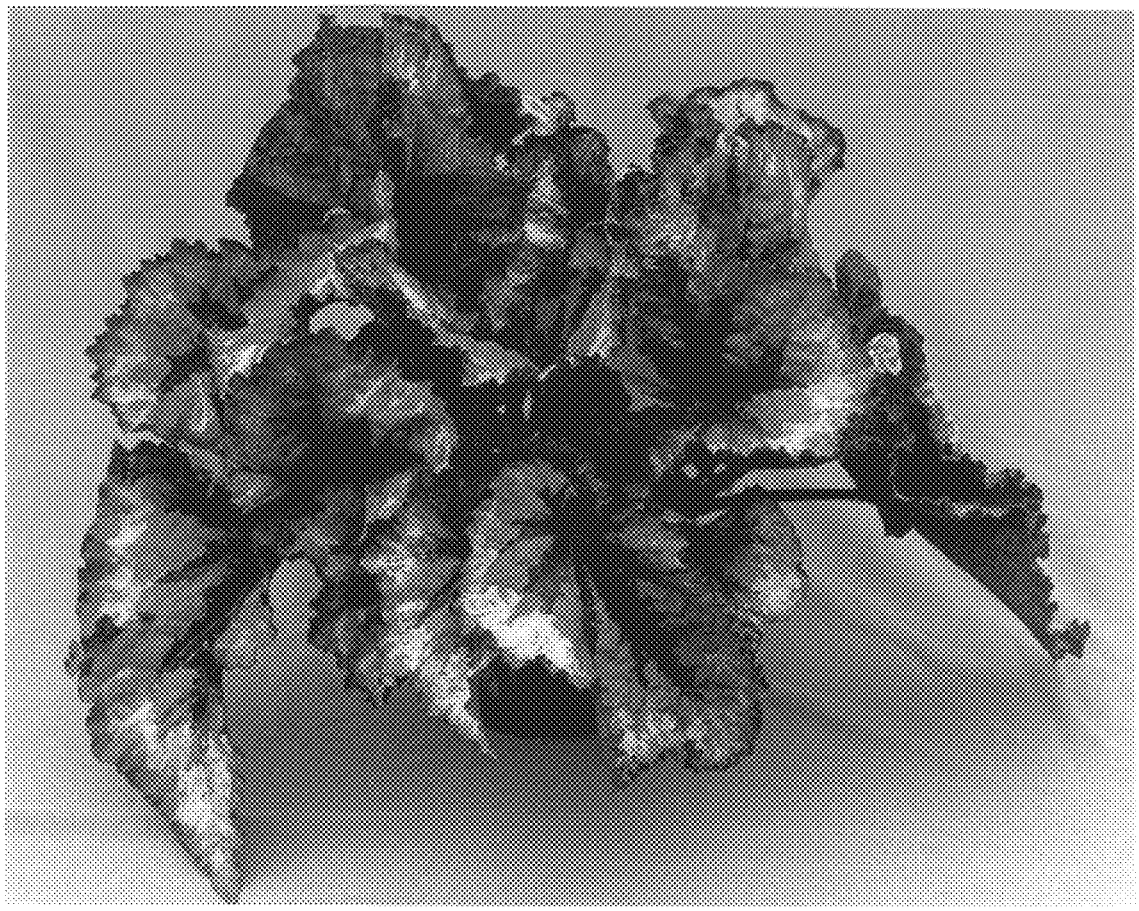

* * * * *